(12) United States Patent
De Polo et al.

(10) Patent No.: US 7,771,392 B2
(45) Date of Patent: Aug. 10, 2010

(54) LEAD SCREW DELIVERY DEVICE USING REUSABLE SHAPE MEMORY ACTUATOR DRIVE

(75) Inventors: Marco C. De Polo, San Mateo, CA (US); Christopher Wiegel, Sunnyvale, CA (US); Steve N. Roe, San Mateo, CA (US)

(73) Assignees: Roche Diagnostics Operations, Inc., Indianapolis, IN (US), part interest; Disetronic Licensing AG, Burgdorf (CH), part interest ( * ) Notice: Subject to any disclaimer, the term of this patent is extended or adjusted under 35 U.S.C. 154(b) by 102 days.

(21) Appl. No.: 11/946,905

(22) Filed: Nov. 29, 2007

(65) Prior Publication Data

US 2009/0143730 A1 Jun. 4, 2009

(51) Int. Cl.
*A61M 1/00* (2006.01)
*A61M 37/00* (2006.01)
(52) U.S. Cl. .................. 604/152; 604/151; 604/131
(58) Field of Classification Search ......... 604/151–155, 604/131, 890.1–892.1
See application file for complete search history.

(56) References Cited

U.S. PATENT DOCUMENTS

| | | | |
|---|---|---|---|
| 5,127,228 A | 7/1992 | Swenson | |
| 5,575,790 A | 11/1996 | Chen et al. | |
| 5,626,566 A * | 5/1997 | Petersen et al. | 604/208 |
| 5,816,306 A | 10/1998 | Giacomel | |
| 6,242,841 B1 | 6/2001 | Williams | |
| 6,375,638 B2 | 4/2002 | Nason et al. | |
| 6,404,098 B1 | 6/2002 | Kayama et al. | |
| 6,656,158 B2 | 12/2003 | Mahoney et al. | |
| 6,656,159 B2 | 12/2003 | Flaherty | |
| 6,684,724 B2 | 2/2004 | Narasimhiah et al. | |
| 6,832,477 B2 | 12/2004 | Gummin et al. | |
| 6,851,260 B2 | 2/2005 | Mernoe | |
| 7,052,251 B2 | 5/2006 | Nason et al. | |
| 7,128,727 B2 | 10/2006 | Flaherty et al. | |
| 7,144,384 B2 | 12/2006 | Gorman et al. | |
| 2001/0016710 A1 | 8/2001 | Nason et al. | |
| 2003/0163099 A1 * | 8/2003 | Wermeling et al. | 604/275 |
| 2003/0199824 A1 | 10/2003 | Mahoney et al. | |
| 2004/0153032 A1 | 8/2004 | Garribotto et al. | |
| 2004/0220551 A1 | 11/2004 | Flaherty et al. | |
| 2005/0192561 A1 * | 9/2005 | Mernoe | 604/890.1 |
| 2005/0238507 A1 | 10/2005 | Dilanni et al. | |

FOREIGN PATENT DOCUMENTS

WO 03089789 10/2003

* cited by examiner

*Primary Examiner*—Nicholas D Lucchesi
*Assistant Examiner*—Leah Stohr
(74) *Attorney, Agent, or Firm*—Dinsmore & Shohl LLP (57) ABSTRACT

A drug delivery device drive that includes a single shape memory alloy wire actuator to advance a lead screw via a ratcheting mechanism and method thereof are disclosed. In one embodiment, a shape memory alloy wire is operably connected to one of a pair of ratchet wheels and configured to drive incrementally the rotation of the connected ratchet wheel via a contraction, which in turn drives the rotation of the other ratchet wheel about a rotational axis which moves a lead screw and advances a plunger to dispense a liquid drug from a drug container. A drug delivery device using the shape memory alloy wire actuator in combination with the ratcheting mechanism to incrementally rotate a shaft, a lead screw or a sleeve provides for a more compact an less complicated design.

20 Claims, 5 Drawing Sheets

LEAD SCREW DELIVERY DEVICE USING REUSABLE SHAPE MEMORY ACTUATOR DRIVE

FIELD OF THE INVENTION

The present invention is related to drug delivery devices, and in particular to a drug delivery device that includes a single shape memory alloy wire actuator drive to advance a lead screw via a ratcheting mechanism.

BACKGROUND OF THE INVENTION

Shape memory alloy (SMA) actuators are used for a wide range of applications. One typically application for SMA actuators is to perform limited displacements which generate work. In such displacement applications, the SMA actuator is typically in the form of a wire that transforms linear motion into incremental relative motion. When applying a current to the cold (low temperature or martensitic state) shape memory alloy (SMA) wire the temperature rises until the transformation temperature is reached (high temperature or austenite state) and due to a crystalline restructuring of the material, a contraction occurs. With such a contraction, force or torque is thus generated. However, it is to be appreciated that after the contraction, the SMA wire does not reset itself and therefore a counterforce has to bring the SMA wire into its original position.

In the field of drug delivery devices, prior art drug delivery systems which use shape memory alloy actuators are typically reset by having opposed SMA wires. Such a configuration allows higher cycle frequencies. However, such a design is more complex and additional space is required for the second SMA wire.

SUMMARY OF THE INVENTION

It is against the above background that the present invention provides a drug delivery device that includes a single shape memory alloy wire actuator to advance a lead screw via a ratcheting mechanism which provides for a more compact and less complicated design.

In a first embodiment, a drive system used to dispense a liquid drug from a drug container having a plunger is disclosed. The drive system comprises a lead screw having a rotational axis and operably connected to the plunger. A ratcheting mechanism having first and second ratchet wheels provided along the rotational axis is also provided. The first ratchet wheel is connected to the lead screw to move the lead screw. A shape memory alloy wire is operably connected to the second ratchet wheel and configured to drive incrementally the rotation of the second ratchet wheel via a contraction, which in turn drives the rotation of the first ratchet wheel about the rotational axis which moves the lead screw and advances the plunger to dispense the liquid drug from the drug container.

In a second embodiment, a method of dispensing a liquid drug from a drug container having a plunger is disclosed. The method comprises operably connecting to the plunger a lead screw having a rotational axis, and providing along the rotational axis a ratcheting mechanism having first and second ratchet wheels. The first ratchet wheel is connected to the lead screw to move the lead screw. The method further includes operably connecting a shape memory alloy wire to the second ratchet wheel, and driving incrementally the rotation of the second ratchet wheel via contracting the shaped memory alloy wire to drive the rotation of the first ratchet wheel about the rotational axis which moves the lead screw and advances the plunger to dispense the liquid drug from the drug container.

These and other features and advantages of the invention will be more fully understood from the following description of various embodiments of the invention taken together with the accompanying drawings.

BRIEF DESCRIPTION OF THE DRAWINGS

The following detailed description of the various embodiments of the present invention can be best understood when read in conjunction with the following drawings, where like structure is indicated with like reference numerals and in which.

DETAILED DESCRIPTION

In the following description of the embodiments of the invention, skilled artisans appreciate that elements in the figures are illustrated for simplicity and clarity and have not necessarily been drawn to scale. For example, the dimensions of some of the elements in the figures may be exaggerated relative to other elements to help to improve understanding of embodiment(s) of the present invention. Accordingly, the drawings are merely schematic representations, intending to depict only typical embodiments of the invention, and therefore should not be considered as limiting the scope of the invention. The invention will be described with additional specificity and detail through the accompanying drawings. The description of the invention may contain, for example, such descriptive terms as up, down, top, bottom, right or left. These terms are meant to provide a general orientation of the parts of the invention and are not meant to be limiting as to the scope of the invention.

Figure 1:
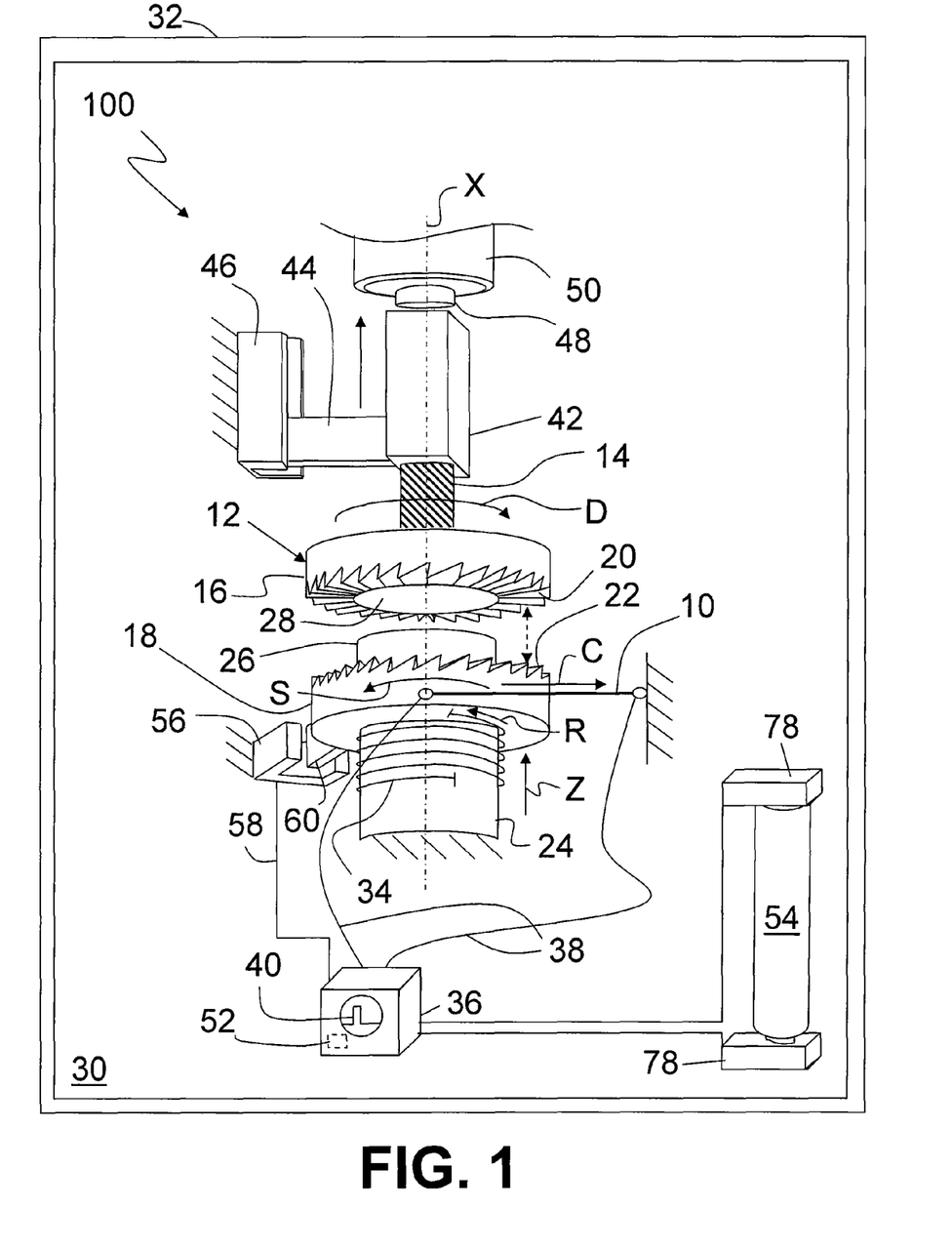
FIG. 1 is a partially exploded, perspective view of a drug delivery pump drive embodiment using a single shape memory alloy wire actuator to advance a lead screw via a ratcheting mechanism having a torsion spring which provides tight engagement between facing ratcheting surfaces and a reset function according to the present invention.

FIG. 1 is a partially exploded perspective view of a first embodiment of a drug delivery pump drive 100 that includes a single Shape Memory Alloy (SMA) wire 10. It is to be appreciated that such a drug delivery pump drive 100 is suitable for use in an infusion pump application to accurately pump a liquid drug. In one embodiment, the pump drive 100 has a 3.5×3.5×15 mm footprint, which is about 20% the size of conventional electrical micro-motors.

In the illustrated embodiment of FIG. 1, the SMA wire 10 is connected to a ratcheting mechanism, generally indicated by symbol 12, which in turn is connected to a lead screw 14. In one embodiment, the ratcheting mechanism 12 comprises first and second ratchet wheels 16, 18 having facing ratcheting surfaces 20, 22 arranged perpendicularly to the lead screw 14. As shown, the first ratchet wheel 16 is fixed to the lead screw 14, and the second ratchet wheel 18 is mounted rotatably to a post 24. As shown, the post 24 extends through the second ratchet wheel 18 and is accommodated at an end 26 in a cavity 28 of the first ratchet wheel 16. In this manner, the first ratchet wheel 16 is also rotatable mounted to the end 26 of the post 24. The post 24 at the other end is fix, such as, to a base 30 of an infusion pump 32.

In one embodiment, the facing ratcheting surfaces 20, 22 are opposing axially extended teeth, such that rotation in a first (drive) direction, indicated by arrow D, the teeth of both ratchet wheels 16, 18 mesh and rotate together, and in a second (return or reset) direction, indicated by symbol S, the teeth of the second ratchet wheel 18 slip or rides over the teeth of the first ratchet wheel 16, such that second ratchet wheel 18 rotates relative to the first ratchet wheel 16 about a rotational axis, indicated by symbol X. Accordingly, the ratcheting mechanism 12 provides a unidirectional ratchet like motion, which rotates the lead screw 14 about the rotational axis X in only the first direction D.

In the illustrated embodiment of FIG. 1, a torsion spring 34 is provided to the post 24 to performs two functions simultaneously, which helps to facilitate a very compact infusion pump design. The first function of the torsion spring 34 is to provide an axial spring force that is applied to the second ratchet wheel 18. The axial spring force is indicated by arrow Z, and maintains a tight engagement between the surfaces 20, 22 of the ratchet wheels 16, 18 in the first (drive) direction D, but which can be overcome in the second direction S via a resetting force, which is discussed hereafter, to permit disengagement between the facing ratcheting surfaces 20, 22 along the rotational axis X, thereby allowing the unidirectional ratchet like motion.

The second function simultaneously provided is that the torsion spring 34 acts as a reset mechanism to reset the SMA wire 10 after a contraction, indicated by symbol C, which rotates the lead screw 14 about the rotational axis X. In particular, the torsion spring 34 stretches the SMA wire 10 back to an original (initial) position via applying a resetting force, which is indicated by symbol R. The resetting force R is provide via a first end (or portion thereof) of the torsion spring 34 being connected to the second ratchet wheel 18, and a second end (or portion thereof) of the torsion spring 34 being mounted to the post 24. Accordingly, rotation of the second ratchet wheel 18 in the first (drive) direction D, which also rotates the first ratchet wheel 16 in the same direction, causes the ends of the torsion spring 34 to move (twist) relative to each other, thereby loading the torsion spring 34 with torque. In this manner, upon removal of the excitation to the SMA wire 10, the torque of the torsion spring 34 counter-rotates the second ratchet wheel 18 about the post 24, thereby returning the SMA wire 10 to its initial (pre-contraction) position.

As shown by FIG. 1, the SMA wire 10 is electrically connected at both ends to a controller 36 via electrical conductors 38. In use, the application of a drive signal 40, such as for example, a current pulse from the controller 36, via the electrical conductors 38, causes the SMA wire 10 to contract due to excitation from the martensitic state to the austenite state. This contraction C causes the second ratchet wheel 18 as well as the first ratchet wheel 16 to rotate incrementally in the first (drive) direction D about the rotational axis X.

As the first ratchet wheel 16 of the ratcheting mechanism 12 is fixed to the lead screw 14, rotation of the ratcheting mechanism in the first (drive) direction D causes the lead screw 14 to also rotate about the rotational axis X. It is to be appreciated that the lead screw 14 is only free to rotate and is prevented from translating axially.

A threaded nut 42 engages the lead screw 14. The threaded nut 42 is provided with a projection or key portion 44 which is situated in a slot or keyway 46 that is mounted, for example, to the base 30 of the infusion pump 32, both of which are illustrated in block diagram for ease of illustration. In this manner, the threaded nut 42 is prevented by the keyway 46 from rotating about the rotational axis X with the ratcheting mechanism 12 and lead screw 14 in the first direction D, but is free to translate incrementally along axis X. The incremental advancement of the threaded nut 42 along the keyway 46 causes a plunger 48 to be pushed into a syringe-like drug cartridge or container 50. The pushing of the plunger 48, via incremental advancement of the threaded nut 42, causes a liquid drug to be expelled from the container 50 in a controlled manner.

In one embodiment, the controller 36 includes capacitor(s) 52 for storing a charge received form a power source 54, in which the drive signal 40 is a single charge. The signal charge from the controller 36 causes the incremental rotation of the ratcheting mechanism 12 and lead screw 14. As mentioned previously above, this rotation advances the plunger 48 into container 50 to dispense a predetermined volume of the drug out of the drug container, such as for example, into the subcutaneous tissue of a patient. A hard stop 56 is provided to ensure that the ratcheting mechanism 12 is incremental rotated a desire amount with each contraction of the SMA wire 10. In this embodiment, the hard stop 56 is also electrically connected to the controller, via electrical conductor 58, and provides a motion feedback signal of the ratcheting mechanism 12. In one embodiment, the hard stop 56 provides the controller 36 the motion feedback signal upon a projection 60 provided by the second ratchet wheel 18 contacting the hard stop 56 due to rotation of the ratcheting mechanism 12 in the first (drive) direction D. In this manner, the hard stop 56 helps to provide accuracy in the dispensing of the liquid drug since accurate displacement of the SMA wire 10 is very difficult to achieve.

Figure 2:
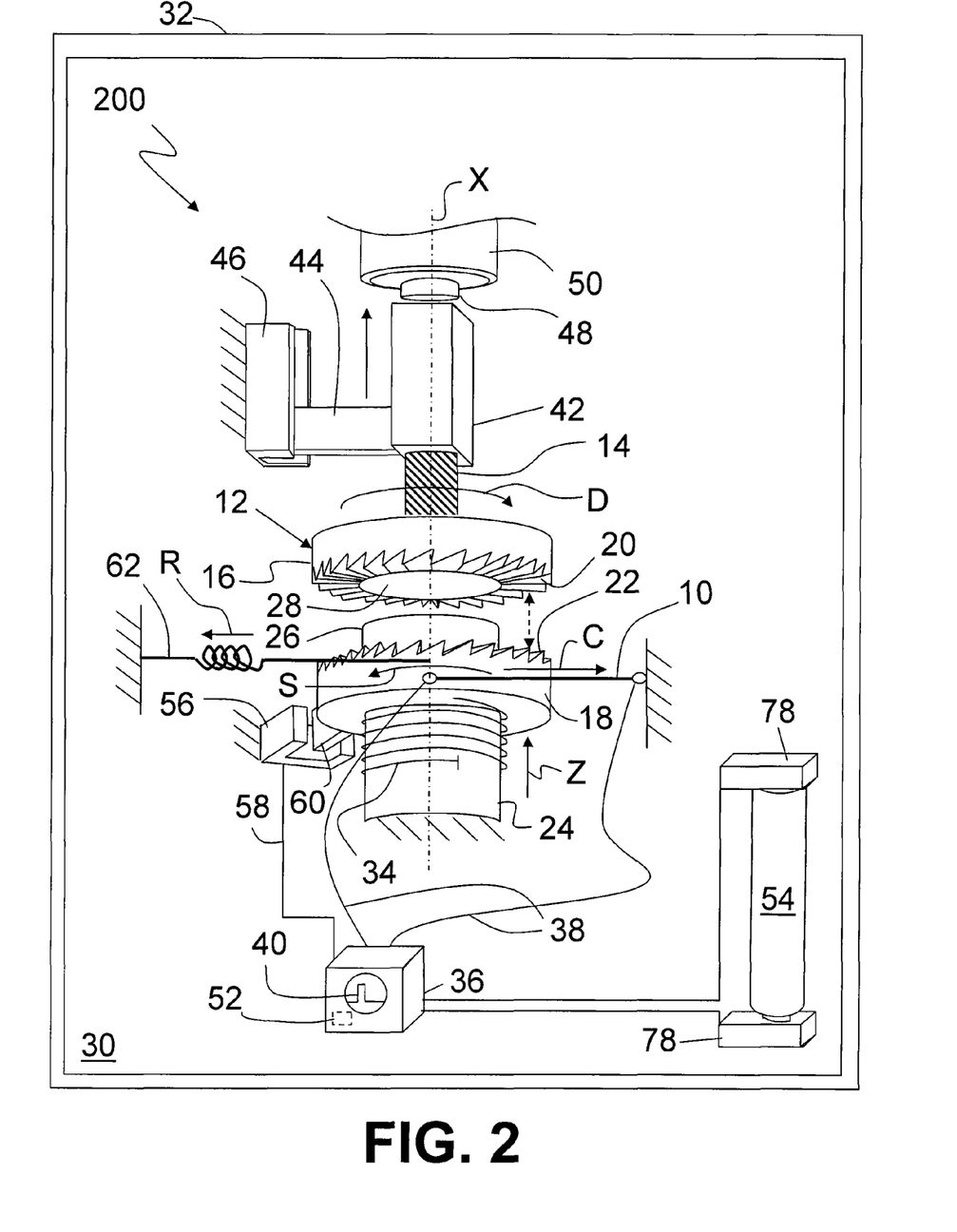
FIG. 2 is a partially exploded, perspective view of another drug delivery pump drive embodiment using a single shape memory alloy wire to advance a lead screw via a ratcheting mechanism having a torsion spring which provides tight engagement between facing ratcheting surfaces and a spring providing a reset function according to the present invention.

FIG. 2 shows another embodiment of a pump drive 200 according to the present invention wherein the torsion spring 34 is not fixed between the second ratchet wheel 18 and post 24 as in the previous embodiment illustrated by FIG. 1. In this alternative embodiment, the second ratchet wheel 18 is rotated by the attached SMA wire 10 in the first (drive) direction D and counter rotated in the second (reset) direction S by a reset spring 62. In this manner, the reset spring 62 takes over the function of the torsion spring 34 of applying the reset force R to the second ratchet wheel 18 to bring the SMA wire 10 back to the initial position after a contraction C. For brevity, as the pump drive 200 advances the plunger 48 in the same manner as described above with reference to the pump drive 100 shown by FIG. 1, no further discussion is provided about this embodiment.

Figure 3:
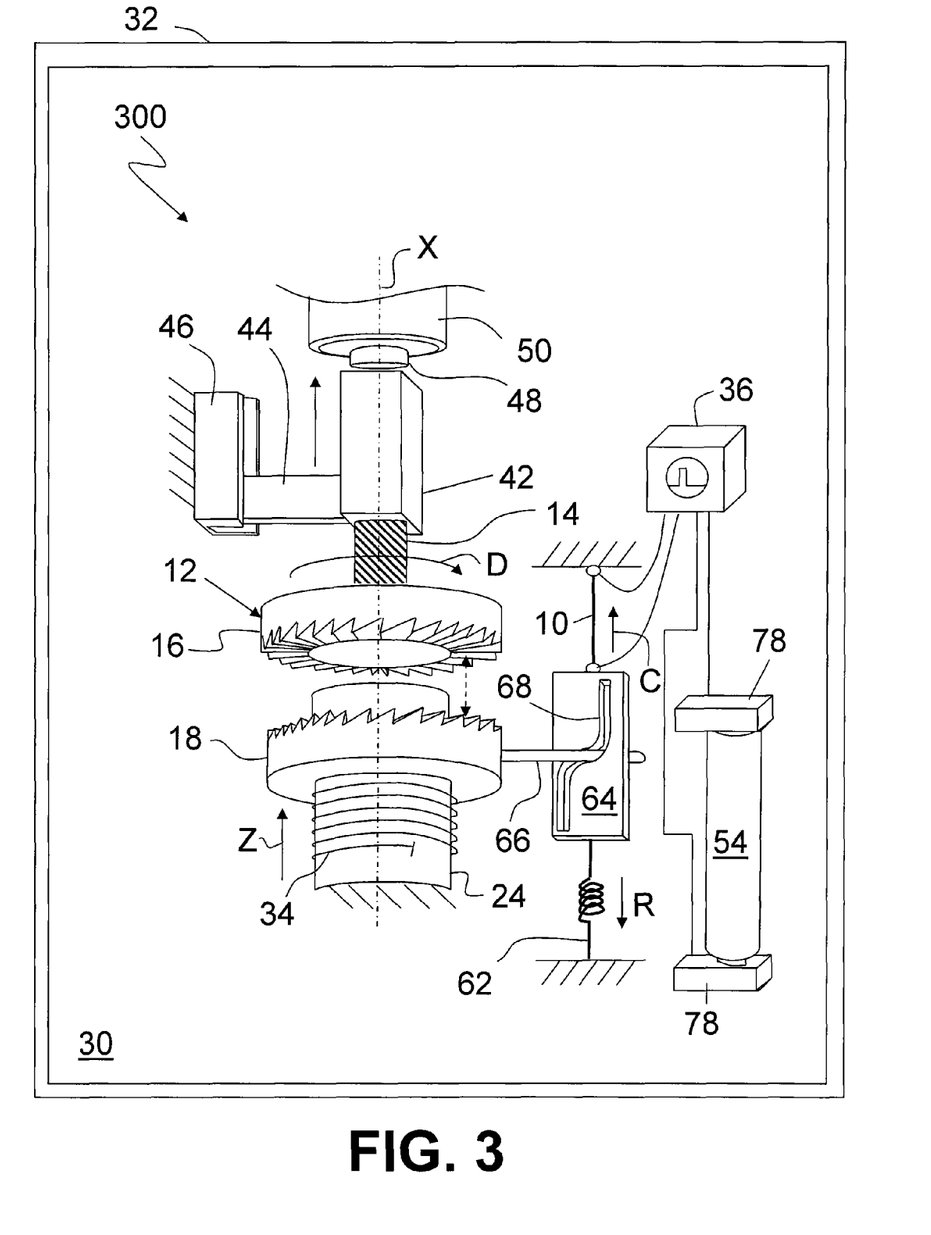
FIG. 3 is a partially exploded, perspective view of a drug delivery pump drive embodiment using a single shape memory alloy wire attached to a slotted sliding mechanism which advances a lead screw via a ratcheting mechanism according to the present invention.

FIG. 3 shows still another embodiment of a pump drive 300 according to the present invention. In this embodiment, the pump drive 300 comprises two ratchet wheels 16, 18 similar to the embodiment of FIG. 1, except that the SMA wire 10 is not directly connected to the second ratchet wheel 18. In this alternative embodiment, the SMA wire 10 is oriented parallel to the rotational axis X, instead of perpendicular as in the previous embodiments, and directly connected to a side of a sliding mechanism 64. The reset spring 62 is connected to another side of the sliding mechanism 64 opposite to the side to which the SMA wire 10 is attached, wherein the torsion spring 34 provides the same function as provided in the embodiment shown by FIG. 2. In this manner, the sliding mechanism 64 performs parallel reciprocating motion to the rotational axis X upon contraction C of the SMA wire 10, and resetting via reset force R being provided by the reset spring 62. This aligned configuration of the SMA wire 10, the reset spring 62, and sliding mechanism 64 allows a compact design since all parts are accommodated close to the ratcheting mechanism 12 and lead screw 14.

To move the ratcheting mechanism 12, via the parallel reciprocating motion of the sliding mechanism 64, the second ratchet wheel 18 provides a pin 66 that fits into a S-curve shaped slot 68 of the sliding mechanism 64. The sliding mechanism 64 is guided parallel to the rotational axis X and when the SMA wire 10 contracts, the sliding mechanism 64 moves axially and the S-curve shaped slot 68 displaces the pin 66 angularly about the rotational axis X. This motion results in an incremental rotation of the ratchet wheels 16, 18 and lead screw 14 in the first direction D and therefore in an incremental axial advancement of the threaded nut 42. For brevity, as the pump drive 300 advances the plunger 48 in the same manner as described above with reference to the pump drive 100 shown by FIG. 1, no further discussion is provided about this embodiment.

Figure 4:
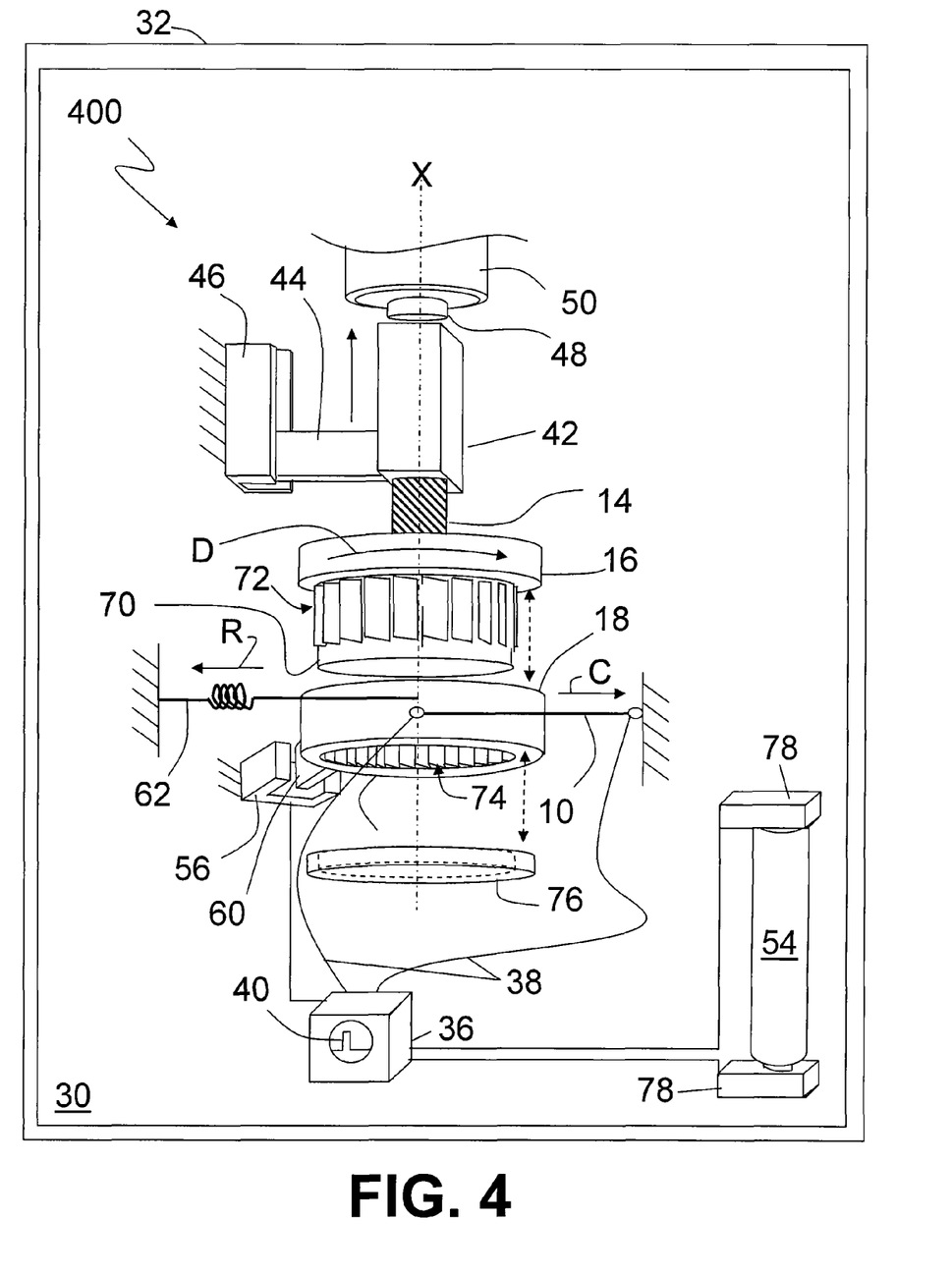
FIG. 4 is a partially exploded, perspective view of another drug delivery pump drive embodiment using a single shape memory alloy wire to advance a lead screw via a ratcheting mechanism according to the present invention.

Another embodiment of a pump drive 400 according to the present invention is shown by FIG. 4, with the same basic arrangement as the embodiment shown by FIG. 2, except for the use of the facing ratcheting surfaces 20 and 22, the post 24, and the torsion spring 34. In this embodiment, the first ratchet wheel 16 is provided with an insert portion 70 providing radially flexible teeth, generally indicated by symbol 72, and the second ratchet wheel 18 is provided as a sleeve having rigid teeth, generally indicated by symbol 74, provided radially on an interior surface thereof. In an alternative embodiment, the flexible teeth 72 may be provided to the second ratchet wheel 18 and the rigid teeth 74 may be provided to the insert portion 70 of the first ratchet wheel 16.

As shown, the insert portion 70 is accommodated in the second ratchet wheel 18 such that the flexible teeth 72 is engaged by the rigid teeth 74 when the second ratchet wheel is rotated in the first (drive) direction D, and the rigid teeth 74 will slip pass the flexible teeth 72 when the second ratchet wheel 18 is rotated in the opposite direction via the resetting force R provided by reset spring 62 after a contraction C of the SMA wire 10. An end cap 76 is mounted rotatably to an end of the insert portion 70 adjacent the second ratchet wheel 18 on the side opposed to the first ratchet wheel 16, to maintain the teeth 72, 74 in axial alignment along the rotational axis X. For brevity, as the pump drive 400 advances the plunger 48 in the same manner as described above with reference to the pump drive 200 shown by FIG. 2, no further discussion is provided about this embodiment.

In all the illustrative pump drive embodiments shown by FIGS. 1-4, the power source 54 is a battery provided to power the infusion pump 32. The power source (i.e., battery) 54 is held between a pair of electrical terminal posts 78 which are wired to provide power to the controller 36. Other electrical component, such as for example, an on/off button 90 (FIG. 5) and a small/large dose selection switch 92 (FIG. 5) may also be provided as input to the controller 36 to provide the stated function to the infusion pump 32.

Figure 5:
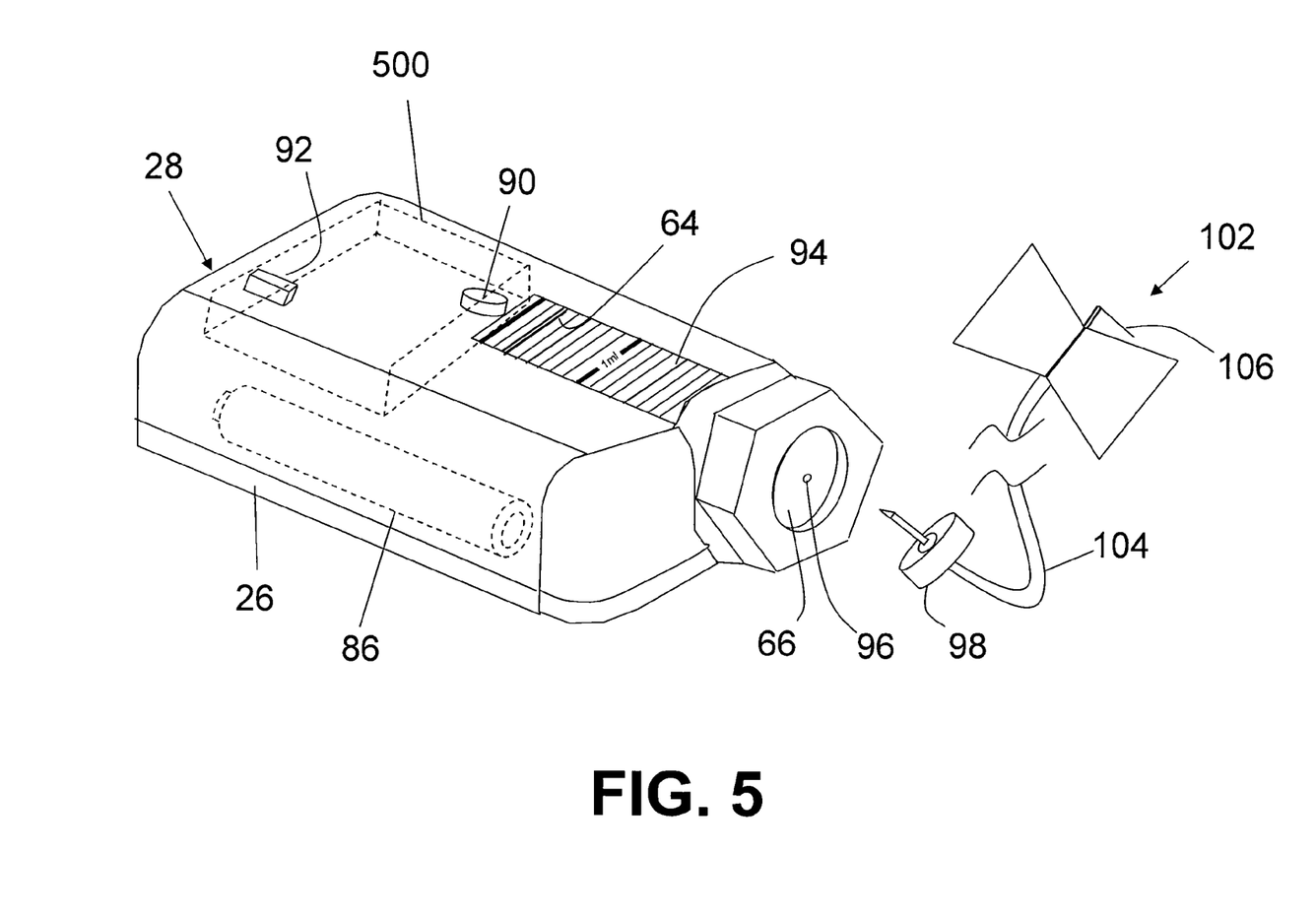
FIG. 5 is a perspective view of a miniature drug delivery pump embodiment using a drug delivery pump drive using a single shape memory alloy wire to advance a lead screw via a ratcheting mechanism to advance a syringe plunger to deliver a liquid drug according to the present invention.

As shown by FIG. 5, a pump drive 500 according to any one of embodiments of the pump drive 100, 200, 300, and 400 shown by FIGS. 1-4, is conveniently used in a miniature drug delivery pump 128. In the illustrated embodiment, the power source 54 is a battery, such as for example a size AAAA, which is about 42.5 mm long and about 8.3 mm in diameter, weighing around 6.5 grams. Output of alkaline batteries in this size is about 1.5 volts, 625 mA·h. Although elements in the figures may be exaggerated in portion to other components, it is to be appreciated that the approximate relative size between the drug deliver pump 128 and the battery is intended to be shown in the embodiment illustrated by FIG. 5. Accordingly, as shown, the miniature drug deliver pump 128 is not much larger than the AAAA battery, and is in one embodiment about 61 mm long, about 32 mm wide, and 15.5 mm in height, and weighs about 32 grams, with the container 50 holding about 2 ml of a liquid drug. Such dimensions of the drug deliver pump 128 is about one third the size of existing conventional drug deliver pumps. The small size of the drug delivery pump 128 due to the reduction in size and components of the pump drive 500 as well as the drive's silent operation, makes it easier for the patient to conceal the drug deliver pump under clothing.

In the illustrated embodiment shown by FIG. 5, the drug delivery pump 128 provides a scaled window 94 through which a portion of plunger 48 is visible and by which the patient may use to meter/monitor the delivery of the liquid drug from the container 50. The container 50 includes an injection site 96 which is used to connect a spike connector 98 of an administration set 102 to the drug deliver pump 128. The spike connector 98 is connected to a fluid conduit 104 which at the distal end connects to a catheter 106, which enters the patient's intravenous system through the skin for delivery of the liquid drug.

Although not limited to, some of the noted advantages of the present invention are as follows: the inherent precision of the motion from the shape memory alloy wire actuator arrangement which can be used to accurately deliver very small doses (i.e., about 100 nL), nearly silent operation, fewer moving parts, and smaller parts. Such advantages result in an overall compact and low cost drug delivery pump for the consumer.

The foregoing description of the invention has been presented for purposes of illustration and description. It is not intended to be exhaustive or to limit the invention to the precise form disclosed, and other modifications and variations may be possible in light of the above teachings. The above embodiments disclosed were chosen and described to explain the principles of the invention and its practical application to thereby enable others skilled in the art to best utilize the invention. It is intended that the appended claims be construed to include other alternative embodiments of the invention except insofar as limited by the prior art.

What is claimed is:

1. A drive system used to dispense a liquid drug from a drug container having a plunger, said drive system comprising:
   a lead screw having a rotational axis and operably connected to the plunger;
   a ratcheting mechanism having first and second ratchet wheels provided along the rotational axis, said first ratchet wheel is connected to the lead screw to move the lead screw; and a shape memory alloy wire operably connected to the second ratchet wheel and configured to drive incrementally the rotation of the second ratchet wheel via a contraction, which in turn drives the rotation of the first ratchet wheel about the rotational axis which moves the lead screw and advances the plunger to dispense the liquid drug from the drug container, and wherein the first and second ratchet wheels provide two opposing ratcheting surfaces with facing axially extended teeth which are spring biased axially for proper engagement via a torsion spring, wherein the torsion spring is also used to reset the shape memory alloy wire after the contraction driving incrementally the rotation of the second ratchet wheel.

2. The drive system according to claim 1, wherein the first and second ratchet wheels are arranged perpendicularly to the lead screw.

3. The drive system according to claim 1, further comprises a post about which the first and second ratchet wheels are mounted rotatably.

4. The drive system according to claim 1, wherein the second ratchet wheel is spring biased radially to reset the shape memory alloy wire after the contraction incrementally driving the rotation of the second ratchet wheel.

5. The drive system according to claim 1, wherein the second ratchet wheel is spring biased radially via a reset spring connected in opposition to the shaped memory alloy wire for resetting the shape memory alloy wire after the contraction incrementally driving the rotation of the second ratchet wheel.

6. The drive system according to claim 1, further comprising a controller electrically connected to the shaped memory alloy to generate the contraction of the shaped memory alloy wire.

7. The drive system according to claim 1, further comprising a controller electrically connected to the shaped memory alloy, and having capacitors for storing a charge used by the controller to generate the contraction of the shaped memory alloy wire.

8. The drive system according to claim 1, further comprising a controller electrically connected to the shaped memory alloy to generate the contraction of the shaped memory alloy wire and a hard stop mechanism electrically connected to the controller and configured to provide motion feedback of the ratchet mechanism.

9. The drive system according to claim 1 provided in a battery operated drug delivery device providing the drug container.

10. The drive system according to claim 1, wherein the first ratchet wheel is provided with an insert portion providing radially flexible teeth, and wherein the second ratchet wheel is provided as a sleeve having rigid teeth provided radially on an interior surface thereof.

11. A drive system used to dispense a liquid drug from a drug container having a plunger, said drive system comprising:
a lead screw having a rotational axis and operably connected to the plunger;
a ratcheting mechanism having first and second ratchet wheels provided along the rotational axis, said first ratchet wheel is connected to the lead screw to move the lead screw; and
a shape memory alloy wire operably connected to the second ratchet wheel and configured to drive incrementally the rotation of the second ratchet wheel via a contraction, which in turn drives the rotation of the first ratchet wheel about the rotational axis which moves the lead screw and advances the plunger to dispense the liquid drug from the drug container,
a post about which the first and second ratchet wheels are mounted rotatably, wherein the second ratchet wheel is spring biased axially on the post towards the first ratchet wheel via a torsion spring, the torsion spring having a first end mounted to the second ratchet wheel and a second end mounted to the post, wherein the torsion spring is configured to reset the shape memory alloy wire after the contraction incrementally driving the rotation of the second ratchet wheel.

12. A drive system used to dispense a liquid drug from a drug container having a plunger, said drive system comprising:
a lead screw having a rotational axis and operably connected to the plunger;
a ratcheting mechanism having first and second ratchet wheels provided along the rotational axis, said first ratchet wheel is connected to the lead screw to move the lead screw, wherein the first and second ratchet wheels provide two opposing ratcheting surfaces with facing axially extended teeth which are spring biased axially for proper engagement via a torsion spring, and the second ratchet wheel is spring biased radially via a reset spring connected in opposition to a shaped memory alloy wire for resetting the shape memory alloy wire after the contraction incrementally driving the rotation of the second ratchet wheel; and
a the shape memory alloy wire operably connected to the second ratchet wheel and configured to drive incrementally the rotation of the second ratchet wheel via a contraction, which in turn drives the rotation of the first ratchet wheel about the rotational axis which moves the lead screw and advances the plunger to dispense the liquid drug from the drug container.

13. A drive system used to dispense a liquid drug from a drug container having a plunger, said drive system comprising:
a lead screw having a rotational axis and operably connected to the plunger;
a ratcheting mechanism having first and second ratchet wheels provided along the rotational axis, said first ratchet wheel is connected to the lead screw to move the lead screw; and a shape memory alloy wire operably connected to the second ratchet wheel and configured to drive incrementally the rotation of the second ratchet wheel via a contraction, which in turn drives the rotation of the first ratchet wheel about the rotational axis which moves the lead screw and advances the plunger to dispense the liquid drug from the drug container; and
a controller electrically connected to the shaped memory alloy to generate the contraction of the shaped memory alloy wire and a hard stop mechanism electrically connected to the controller and configured to provide motion feedback of the ratchet mechanism.

14. A method of dispensing a liquid drug from a drug container having a plunger, said method comprises:
operably connecting to the plunger a lead screw having a rotational axis;
providing along the rotational axis a ratcheting mechanism having first and second ratchet wheels, said first ratchet wheel being connected to the lead screw to move the lead screw, wherein the first and second ratchet wheels provide two opposing ratcheting surfaces with facing axial extended teeth, said method further comprising using a torsion spring to spring biased the two opposing ratcheting surfaces for proper engagement of the facing axially extended teeth, and to reset a shape memory alloy wire after the contraction driving incrementally the rotation of the second ratchet wheel;
operably connecting the shape memory alloy wire to the second ratchet wheel; and driving incrementally the rotation of the second ratchet wheel via contracting the shaped memory alloy wire to drive the rotation of the first ratchet wheel about the rotational axis which moves the lead screw and advances the plunger to dispense the liquid drug from the drug container.

15. The drive system according to claim 11, further comprising a controller electrically connected to the shaped memory alloy to generate the contraction of the shaped memory alloy wire.

16. The drive system according to claim 11, further comprising a controller electrically connected to the shaped memory alloy, and having capacitors for storing a charge used by the controller to generate the contraction of the shaped memory alloy wire.

17. The drive system according to claim 11, further comprising a controller electrically connected to the shaped memory alloy to generate the contraction of the shaped memory alloy wire and a hard stop mechanism electrically connected to the controller and configured to provide motion feedback of the ratchet mechanism.

18. The drive system according to claim 11, wherein the first and second ratchet wheels are arranged perpendicularly to the lead screw.

19. The drive system according to claim 11, wherein the second ratchet wheel is spring biased radially to reset the shape memory alloy wire after the contraction incrementally driving the rotation of the second ratchet wheel.

20. The drive system according to claim 11, wherein the second ratchet wheel is spring biased radially via a reset spring connected in opposition to the shaped memory alloy wire for resetting the shape memory alloy wire after the contraction incrementally driving the rotation of the second ratchet wheel.

* * * * *